United States Patent [19]

Shishikura et al.

[11] Patent Number: 5,349,084
[45] Date of Patent: Sep. 20, 1994

[54] PROCESS FOR RECOVERING HIGH-PURITY ORGANIC ACID

[75] Inventors: Akihiro Shishikura, Sodegaura; Hiroshi Kimbara, Tokyo; Katsuhisa Yamaguchi, Sodegaura; Kunio Arai, Sendai, all of Japan

[73] Assignee: Idemitsu Petrochemical Co., Ltd., Tokyo, Japan

[21] Appl. No.: 765,582

[22] Filed: Sep. 25, 1991

[30] Foreign Application Priority Data

Sep. 28, 1990 [JP] Japan ................................. 2-259828

[51] Int. Cl.⁵ .............................................. C07C 51/42
[52] U.S. Cl. ................................... 562/580; 562/582; 562/584; 562/589; 562/593; 562/585; 562/607; 562/608
[58] Field of Search ............... 562/580, 582, 584, 589, 562/593, 585, 608, 607

[56] References Cited

U.S. PATENT DOCUMENTS

| | | | |
|---|---|---|---|
| 26,415 | 11/1907 | Noerdlinger et al. | 562/580 |
| 2,710,880 | 6/1955 | Filachione et al. | 562/580 |
| 4,250,331 | 2/1981 | Shimshick | 562/485 |

FOREIGN PATENT DOCUMENTS

| | | | |
|---|---|---|---|
| 688245 | 6/1964 | Canada | 562/580 |
| 0016899 | 10/1980 | European Pat. Off. | 562/580 |
| 43618 | 12/1960 | Poland | 562/580 |
| 537712 | 9/1946 | United Kingdom | 562/580 |

OTHER PUBLICATIONS

Patent Abstracts of Japan, vol. 14, No. 254 (C-274) (4197), 31 May 1990 of JP-A-2-72,138 (Res. Assoc. Util. of Light Oil) 12 Mar. 1990.

*Primary Examiner*—José G. Dees
*Assistant Examiner*—Keith MacMillan
*Attorney, Agent, or Firm*—Frishauf, Holtz, Goodman & Woodward

[57] ABSTRACT

The present invention relates to a process for inexpensively and effectively recovering a high-purity organic acid, according to which a crude organic acid is subjected to extraction treatment with an organic solvent to obtain an organic solvent extract containing an organic acid; the organic solvent extract is mixed with a high-pressure gas to precipitate and separate impurities thereby obtaining a solution containing a high-purity organic acid; and the organic acid is separated from the solution to obtain a high-purity organic acid.

19 Claims, No Drawings

PROCESS FOR RECOVERING HIGH-PURITY ORGANIC ACID

BACKGROUND OF THE INVENTION

1. Field of the Invention

The present invention relates to a process for recovering a high-purity organic acid.

2. Description of Prior Art

For separating an organic acid from a crude organic acid which mainly contains citric acid, produced by a fermentation method, and purifying the organic acid, the following process is conventionally known. That is, a metal hydroxide (e.g., calcium hydroxide) is added to an aqueous solution of an organic acid obtained by extraction of fermented koji (fermented grain) with hot water to precipitate a metal salt of the organic acid (e.g., calcium salt), and the mixture containing the precipitate is filtered to obtain the metal salt of the organic acid. Thereafter, the metal salt of the organic acid is suspended in water, and sulfuric acid is added to the suspension to obtain a free organic acid and a precipitate of a metal sulfate (e.g., calcium sulfate). Then, the mixture containing the precipitate is filtered to obtain a filtrate containing free organic acid. Thereafter, the filtrate is subjected to an ion-exchange treatment, treated with activated carbon, and concentrated. The concentrated filtrate was recrystallized several times, and the resultant crystal is dried to obtain the organic acid. However, this conventional process has problems in that (a) large amounts of reagents such as calcium hydroxide, sulfuric acid, etc., are required, (b) the steps are complicated and the treatments take a long period of time, and (c) the process is mainly carried out by means of batches and columns so that the process is not continuously operable. As a result, the cost for the recovery of an organic acid inevitably increases, and the continuous treatment of a large amount of a crude organic acid is impossible.

SUMMARY OF THE INVENTION

It is therefore an object of the present invention to provide a process which can overcome the above problems and can permit efficient recovery of a high-purity organic acid from a crude organic acid at a low cost.

The process for recovering a high-purity organic acid, which is provided by the present invention and which achieves the above object, comprises subjecting a crude organic acid to extraction treatment with an organic solvent to obtain an organic solvent extract containing an organic acid; mixing the organic solvent extract with a high-pressure gas to precipitate and separate impurities thereby obtaining a solution containing a high-puirty organic acid; and separating the organic acid from the solution.

DETAILED DESCRIPTION OF THE INVENTION

The present invention will be detailed hereinafter.

In the process for recovering a high-purity organic acid, provided by the present invention, the crude organic acid used as a starting material refers to a mixture containing an organic acid to be recovered. Specific examples thereof are fermented koji (fermented grain) obtained by surface-fermentation of starch pulp or molasses in the presence of a microorganism of a known fungus genus (to be referred to as "crude organic acid (a)" hereinafter); an organic acid aqueous solution obtained by subjecting the above crude organic acid (a) to extraction with hot water (to be referred to as "crude organic acid (b)" hereinafter); a broth of submerged fermentation obtained by submerged fermentation of starch pulp or molasses in the presence of a microorganism of a known fungus genus (to be referred to as "crude organic acid (c)" hereinafter); and the like. These crude organic acids (a), (b) and (c) generally contain 0.5 to 50% by weight of an organic acid. Examples of such an organic acid are carboxylic acids having 3 to 20 carbon atoms such as citric acid, malic acid, lactic acid, etc.

In addition, the crude organic acids (a), (b) and (c) contain, for example, about 65% by weight of water, about 80% by weight of water and 80% by weight of water, respectively. The water has a great influence on the extraction treatment with an organic solvent and the treatment with a high-pressure gas, which are employed in the process of the present invention for recovering a high-purity organic acid. That is, when the water content is smaller, the extraction treatment with an organic solvent can give an extract having a smaller amount of impurities, and a large amount of a gas is not required for the treatment with a high-pressure gas, i.e., the treatment can be carried out at a lower pressure. Therefore, it is preferred to decrease the water content in advance of carrying out the process.

Although any one of conventionally known drying or concentration methods may be used as a method to decrease the water content, it is preferred to employ a drying or concentration method using a reduced pressure or vacuum. The drying or concentration at a temperature higher than 100° C. is not preferred, since an organic acid may possibly undergo a side reaction with impurities. The drying or concentration is carried out preferably at a temperature between about 40° C. and about 80° C. In this drying or concentration treatment, the crude organic acid (a) (fermented koji or grain) is dehydrated preferably to a water content of about 3 to 30% by weight, and the crude organic acid (b) (organic acid aqueous solution) and the crude organic acid (c) (broth of submerged fermentation) are dehydrated preferably to a water content of 3 to 40% by weight.

An organic acid mixture obtained by a synthesis method may be used as a crude organic acid.

The process of the present invention for recovering a high-purity organic acid uses the above crude organic acid as a starting material, and comprises subjecting a crude organic acid to extraction treatment with an organic solvent to obtain an organic solvent extract containing an organic acid; mixing the organic solvent extract with a high-pressure gas to precipitate and separate impurities thereby obtaining a solution containing a high-purity organic acid; and separating the organic acid from the solution.

First of all, the extraction treatment with an organic solvent will be explained.

In this extraction treatment, an organic solvent is added to the crude organic acid, and an organic acid is extracted, for example, at 20° to 40° C. The organic solvent is selected from alcohols such as methanol, ethanol, propanol, isopropanol, butanol, etc., ketones such as acetone, methyl ethyl ketone, etc., and ethers such as diethyl ether, petroleum ether, etc. These organic solvents may be used alone or in combination. In view of dissolving power and an ease in removal by distillation after the extraction, methanol, ethanol and acetone are particularly suitable. The amount of the organic solvent for use is preferably 2 to 20 times the amount of the dehydrated (dried or concentrated) crude organic acid. The amount of the organic solvent is changed depending upon the water content of the crude organic acid which is dried or concentrated. That is, the amount of the organic solvent is adjusted to obtain a water content, in the organic solvent extract, of about 0.5 to about 20%, preferably 3 to about 15%.

In order to separate impurities (saccharose, proteins) as a precipitate, the above extraction treatment requires about 0.5 to 3 hours of a residence time or a standing time after the organic solvent is added to and mixed with the crude organic acid. After this extraction treatment with an organic solvent, the precipitate of impurities is separated by filtration, whereby an organic solvent extract containing an organic acid is obtained.

One embodiment of the composition of the extract obtainable as above is as follows. The extract contains about 2% to about 35% of a solid content composed mainly of an organic acid, about 0.5% to about 20% of water, and a remainder composed mainly of an organic solvent. The above solid content is present dissolved in the extract. Since, however, this extract contains, as impurities, a large amount of saccharides consisting mainly of disaccharide and trisaccharide, the purity (content) of an organic acid in the solid content (solute concentration) is merely about 60% to about 90%.

Therefore, a purification step is required to increase the purity of an organic acid. According to the present invention, there are carried out steps for this purification in which the above organic solvent extract is mixed with a high-pressure gas to precipitate and separate impurities thereby obtaining a solution containing a high-purity organic acid, and then the organic acid is separated from the solution.

The high-pressure gas to be mixed with the organic solvent extract is preferably a hydrophobic and low-polarity high-pressure gas having a pressure not higher than the critical pressure. Such a high-pressure gas is selected, for example, from $CO_2$, ethylene, propylene, $N_2O$ (laughing gas), fluoromethane, etc. A high-pressure gas having a pressure in the vicinity of the critical pressure may be also used. When the above hydrophobic and low-polarity high-pressure gas having a pressure not higher than the critical pressure is mixed with the organic solvent extract, the high-pressure gas is dissolved in the extract thereby to convert the organic solvent in the extract to a poor solvent. As a result, impurities such as proteins, amino acid, saccharides, etc, which have a lower solubility than an organic acid are precipitated. The above mixing is preferably carried out, e.g., in a mixing tank, and the temperature as one of the mixing conditions is preferably between about 0° C. and about 80° C. The pressure is not higher than the critical pressure, and between about 1 kg/cm$^2$G and about 150 kg/cm$^2$G. That is, the present invention does not require any pressure exceeding 150 kg/cm$^2$G, which is usually used for the extraction with a supercritical fluid. And, it is satisfactory in the present invention to use a pressure necessary to dissolve a gas, which is required for the precipitation of impurities, in the organic solvent extract. When, for example, $CO_2$ is used, it is satisfactory to use a pressure sufficient to dissolve 0.1 to 50% by weight of a $CO_2$ gas in the organic solvent extract, e.g., the pressure between 5 kg/cm$^2$G and 70 kg/cm$^2$G. Further, the high-pressure gas/organic solvent extract weight ratio is preferably about 0.1/1 to about 5/1. The precipitation of the impurities is also affected by the concentration of the impurities in the extract and the water content in the extract. According as the concentration of the impurities increases and according as the water content decreases, the precipitation of the impurities starts at a lower pressure.

Thereafter, the mixture containing a precipitate of the impurities is transferred to a stationary tank and allowed to stand under the gas pressure approximately for 3 to 60 minutes to sediment the precipitated impurities, and the supernatant is obtained. The supernatant comprises a solution of a high-purity organic acid in the organic solvent. The gas used is discharged from the top of the stationary tank and recycled as required.

The pressure of the above-obtained supernatant containing a high concentration of an organic acid is brought back to atmospheric pressure, and the supernatant is optionally decolorized, e.g., with a column packed with an activated carbon. Thereafter, the organic acid is crystallized according to a conventional method, and the resultant organic acid crystal is dried according to a conventional method, whereby the high-purity organic acid as the intended product in the process of the present invention is obtained. The purity of the organic acid obtained differs depending upon the organic acid purity (content) in the crude organic acid used as a starting material. In any case, the purity of the product is remarkably higher than the organic acid purity (content) in its crude organic acid, and for example, the organic acid obtained has a purity of 90% or higher.

The process using a combination of the extraction treatment with the organic solvent and the treatment by mixing the organic acid extract with the high-pressure gas, provided by the present invention, has the following advantages.

(i) The process basically comprises two steps of the extraction with the organic solvent and the mixing with the high-pressure gas, and an organic acid can be separated at high yields by a simple process.

(ii) Since the process obviates reagents such as calcium hydroxide, sulfuric acid, etc., used in conventional processes, the cost can be decreased, and the amount of wastes is small.

(iii) Since the two steps can be carried out continuously, the size of the facilities can be decreased, and a large amount of an organic acid can be continuously recovered for a short period of time.

(iv) Since the treatment by mixing the organic solvent extract with the high-pressure gas is carried out at a relatively low temperature in an oxygen-free atmosphere, no organic acid undergoes a side reaction.

(v) The high-pressure gas used for the treatment by mixing the organic solvent extract with the high-pressure gas can be easily separated, and recycled.

The present invention will be further explained by reference to the Examples to which, however, the present invention shall not be limited. In the following Examples, the term "%" means a percent by weight.

EXAMPLE 1

Five kilograms of citric acid fermented koji or grain as a crude organic acid was dried under vacuum to give 1.702 kg of a dry fermented koji or grain (citric acid 36.3%, water content 7.29%). This fermented koji or grain was charged, 0.5 kg each, into three containers, and subjected to extraction treatment with 2.5 kg of methanol, ethanol or acetone as an organic solvent for 30 minutes. Then, each portion was filtered to give an organic solvent extract containing citric acid. Table 1 shows the characteristics of the organic solvent extracts. The citric acid recoveries were 97 to 99%.

TABLE 1

| Organic solvent | Specific gravity of the extract (g/ml) | Solid content in the extract (%) | Citric acid concentration in solid content (%) |
| --- | --- | --- | --- |
| Methanol | 0.89 | 23.8 | 69.4 |
| Ethanol | 0.89 | 21.8 | 77.9 |
| Acetone | 0.83 | 16.9 | 87.4 |

A $CO_2$ gas was mixed with each of the above-obtained organic solvent extracts at 40° C. at a pressure of 40 to 80 $kg/cm^2G$. The flow rate of each organic solvent extract was 2.0 g/min., and that of $CO_2$ was 1.5 g/min. Then, the resultant mixture liquids were allowed to stand for 3 minutes to precipitate and separate impurities, and thereafter, supernatants were obtained. Table 2 shows the pressures when the organic solvent extracts were individually mixed with the high-pressure gas, each of solid contents in the supernatants recovered from the overflow line, citric acid concentrations in the solid contents, and recoveries of the citric acids.

TABLE 2

| Organic solvent | Pressure ($kg/cm^2G$) | Solid content (%) | Citric acid concentration in solid content (%) | Recovery of citric acid (%) |
| --- | --- | --- | --- | --- |
| Methanol | 50 | 16.8 | 97.3 | 98.9 |
|  | 80 | 17.3 | 91.8 | 96.2 |
| Ethanol | 60 | 16.7 | 99.0 | 97.4 |
|  | 75 | 18.1 | 92.6 | 98.7 |
|  | 80 | 18.9 | 89.1 | 99.2 |
| Acetone | 40 | 14.7 | 99.8 | 99.3 |
|  | 59 | 14.5 | 98.4 | 96.6 |
|  | 77 | 15.3 | 94.6 | 98.0 |
|  | 80 | 15.8 | 92.4 | 88.8 |

The supernatants of which the solid contents, the citric acid concentrations in the solid contents and the citric acid recoveries are shown in Table 2 were sampled in an amount of 50 ml each, and the samples were individually treated with a column packed with 0.5 g of activated carbon, and recrystallized once each to give colorless and transparent citric acid crystals. All of these citric acid crystals had a purity of as high as 99.1 to 99.9%. All of the citric acid crystals recovered were odorless. Further, the entire processes were completed in 2 to 3 hours, which shows that the process of the present invention is remarkably effective as compared with the requirement of at least 10 hours in conventional processes.

EXAMPLE 2

20 Liters of an aqueous solution of fermented citric acid extracted with hot water was used as a crude organic acid. This solution was concentrated at 60° C. with an evaporator to give 4.437 kg of a concentrate containing 56.8% of citric acid and 10.8% of a water content. Two containers were respectively charged with 1.0 kg of the concentrate, and the concentrate was subjected to the extraction treatment with 2.5 kg of ethanol or acetone as an organic solvent, whereby organic solvent extracts containing citric acid were obtained in the same manner as in Example 1. Table 3 shows the specific gravities and solid contents of the organic solvent extracts obtained and citric acid concentrations in the solid contents.

TABLE 3

| Organic solvent | Specific gravity (g/ml) | Solid content (%) | Citric acid concentration in solid content (%) |
| --- | --- | --- | --- |
| Ethanol | 0.86 | 20.7 | 73.1 |
| Acetone | 0.82 | 18.4 | 82.4 |

The organic solvent extracts of which the specific gravity, solid contents and citric acid concentrations in the solid contents are shown in Table 3 were treated with $N_2O$ (laughing gas), ethylene, propane and fluoromethane (Fron) under the conditions of 40° C. and 20 to 110 $kg/cm^2G$ in the same manner as in Example 1 to precipitate and separate impurities, and supernatants were recovered from overflow lines. Table 4 shows the kinds of the gases mixed with the organic solvent extracts pressures when the organic solvent extracts were mixed with the gases, solid contents in the supernatants, citric acid concentrations in the solid contents and citric acid recoveries.

TABLE 4

| Organic solvent | Gas | Pressure ($kg/cm^2G$) | Solid content (%) | Citric acid concentration in solid content (%) | Recovery of citric acid (%) |
| --- | --- | --- | --- | --- | --- |
| Ethanol | $N_2O$ | 53 | 15.6 | 93.8 | 96.7 |
|  | Ethylene | 60 | 16.2 | 89.7 | 96.0 |
|  | Propane | 85 | 15.9 | 92.6 | 97.3 |
|  | Fluoromethane | 74 | 14.9 | 94.3 | 92.9 |
| Acetone | $N_2O$ | 48 | 14.7 | 98.1 | 95.1 |
|  | Ethylene | 71 | 15.2 | 94.6 | 94.8 |
|  | Propane | 68 | 15.3 | 97.2 | 98.1 |
|  | Fluoromethane | 49 | 15.6 | 95.4 | 98.2 |

Fifty milliliters of each of the supernatants of which the solid contents, the citric acid concentrations in the solid contents and the citric acid recoveries are shown in Table 4 was treated with a column packed with 0.5 g of activated carbon, concentrated to 3 ml, and recrystallized. All of the above supernatant liquids gave colorless and transparent citric acid crystals. These crystals had a purity in the range of from 97.6 to 99.8%.

EXAMPLE 3

Five liters of a solution of a liquid-cultured citric acid as a crude organic acid was filtered to remove microogranisms, and then concentrated in the same manner as in Example 2 up to 56.4% of citric acid and 6.38% of a water content. The resultant concentrate in an amount of 0.5 kg out of the total 1.07 kg was subjected to extraction with 0.8 kg of acetone as an organic solvent, and the extraction mixture was filtered to give an extract containing citric acid. The extract obtained by the extraction with acetone had a specific gravity of 0.822 g/ml, a solid content of 30.3% and a citric acid concentration, in the solid content, of 81.6%. A $CO_2$ gas was mixed with the above extract at 35° C. at a pressure of 38 $kg/cm^2G$ in the same manner as in Example 1. After impurities were precipitated and separated, the supernatant was recovered, treated with activated carbon and subjected to crystallization treatment to give 0.1592 kg of a white citric acid crystal. This citric acid crystal had a purity of 99.8%, and the recovery of the citric acid was 92.4%.

EXAMPLE 4

300 Grams of malic acid, 50 g of glucose, 7 g of ammonium sulfate, 3 g of magnesium sulfate, 5 g of corn steep liquor and 5,000 g of water were mixed to prepare a model broth of malic acid. The malic acid had a purity of 82.2%. The fermentation solution model was concentrated with an evaporator at 75° C. until it showed a water content of 13.4%, and the resultant concentrate was cooled to room temperature. 2,000 Grams of acetone was divided into two portions, and these two portions were added to the concentrate separately to extract malic acid and prepare an acetone solution of crude malic acid. This acetone solution of crude malic acid had a composition consisting of 12.8% of a solute concentration, 11.4% of malic acid, 1.4% of glucose, 0.1% of others and the rest of acetone. This extraction with acetone gave malic acid having a purity of 89.1%.

The above acetone solution of crude malic acid was mixed with carbon dioxide under the conditions of 25° C. and 22 kg/cm²G, and impurities were precipitated. And, the impurities precipitated were coagulated with carbon dioxide bubbles under flocculation for about 10 minutes and then, separated by allowing the acetone solution to stand for 20 minutes. The resultant supernatant was recovered. The supernatant had a solute concentration of 11.5% and a malic acid concentration of 11.3%, and the purity of the malic acid increased up to 98.3%. In this case, the precipitate was almost all glucose.

EXAMPLE 5

250 Grams of a commercially available 70% lactic acid, 150 g of glucose and 3 g of a mineral mixture for fermentation were dissolved in 5,000 g of water to prepare a model broth of lactic acid. The model broth was concentrated at 75° C. with an evaporator up to a water content of 9.6%, and cooled to room temperature. 1,000 Grams of ethanol was added to the entire amount of the resultant concentrate to extract lactic acid and prepare an ethanol solution of crude lactic acid. The ethanol solution of crude lactic acid had a composition consisting of 12.8% of lactic acid, 6.8% of glucose, 0.1% of others and the rest of the solvent. The lactic acid had a purity of 65.0%.

The above ethanol solution of crude lactic acid was mixed with carbon dioxide under conditions of 8° C. and 15 kg/cm²G or conditions of 25° C. and 26 kg/cm²G to precipitate impurities. The impurities were coagulated under flocculation for 4 minutes and separated by allowing the ethanol solution to stand for 30 minutes, and then the resultant supernatant liquid was recovered. Table 5 shows the composition of the supernatant obtained in each of the cases under the above conditions. In each case, a high purification degree was obtained. In each of the cases under the above conditions, the precipitate was composed mainly of glucose.

TABLE 5

| Treatment conditions | Lactic acid concentration | Glucose concentration | Purity of lactic acid | Recovery |
|---|---|---|---|---|
| Model broth | 12.8% | 6.8% | 65.0% | — |
| 8° C., 15 kg/cm²G | 11.9% | 1.1% | 91.5% | 93.0% |
| 25° C., 26 kg/cm²G | 12.6% | 0.7% | 94.7% | 98.4% |

According to the present invention, there is provided a process for inexpensively and effectively recovering a high-purity organic acid from a crude organic acid.

What is claimed is:

1. A process for recovering a high-purity organic acid, which comprises
   (a) subjecting a crude organic acid mixture comprising an organic acid, said organic acid comprising a carboxylic acid having 3 to 20 carbon atoms which is a product of a fermentation process, to an extraction treatment with an organic solvent selected from the group consisting of alcohols, ketones and ethers to obtain an organic solvent extract containing the organic acid;
   (b) mixing the organic solvent extract with a high-pressure gas, said high pressure gas having a pressure not higher than critical pressure, said high pressure gas being selected from the group consisting of $CO_2$, ethylene, propylene, $N_2O$ and fluoromethane to precipitate and separate impurities, thereby obtaining a solution containing a high-purity organic acid; and
   (c) separating the organic acid from the solution.

2. The process according to claim 1, wherein the crude organic acid is at least one member selected from the group consisting of fermented koji or grain obtained by surface-fermentation of starch pulp or molasses in the presence of a microorganism of a known fungus genus; an organic acid aqueous solution obtained by subjecting the above fermented koji or grain to extraction with hot water; and a broth of submerged fermentation obtained by submerged fermentation of starch pulp or molasses in the presence of a microorganism of a known fungus genus.

3. The process according to claim 1, wherein the crude organic acid contains 0.5 to 50% by weight of an organic acid.

4. The process according to claim 1, wherein the carboxylic acid is at least one member selected from the group consisting of citric acid, malic acid and lactic acid.

5. The process according to claim 2, wherein the fermented koji or grain as a crude organic acid is dehydrated to a water content of 3 to 30% by weight before the extraction treatment with an organic solvent.

6. The process according to claim 2, wherein the organic acid aqueous solution or the broth of submerged fermentation as a crude organic acid is dehydrated to a water content of 3 to 30% by weight before the extraction treatment with an organic solvent.

7. The process according to claim 1, wherein the extraction treatment with an organic solvent is carried out at a temperature between 20° C. and 40° C.

8. The process according to claim 5 or 6, wherein the organic solvent is used in an amount which is 2 to 20 times as large as that of a dehydrated organic acid.

9. The process according to claim 1, wherein the impurities formed are separated by filtration after the extraction treatment with an organic solvent.

10. The process according to claim 1, wherein the high-pressure gas to be mixed with the organic solvent extract is a hydrophobic and low-polarity high-pressure gas.

11. The process according to claim 1, wherein the organic solvent extract and the high-pressure gas are mixed at a temperature between 0° C. and 80° C.

12. The process according to claim 1, wherein the organic solvent extract and the high-pressure gas are mixed at a pressure which is between 1 kg/cm$^2$G and 150 kg/cm$^2$G.

13. The process according to claim 1, wherein the high-pressure gas and the organic solvent extract have a high-pressure gas/organic solvent extract weight ratio of 0.1/1 to 5/1.

14. The process according to claim 1, wherein the organic solvent is at least one alcohol selected from the group consisting of methanol, ethanol, propanol, isopropanol and butanol.

15. The process according to claim 1, wherein the organic solvent is at least one ketone selected from the group consisting of acetone and methylethylketone.

16. The process according to claim 1, wherein the organic solvent is at least one ether selected from the group consisting of diethylether and petroleum ether.

17. The process according to claim 3, wherein the carboxylic acid is selected from the group consisting of citric acid, malic acid and lactic acid; the extraction treatment is carried out at a temperature of 20° C. to 40° C.; the organic solvent extract and the high-pressure gas are mixed at a temperature of 0° C. to 80° C. and at a pressure which is not higher than critical pressure and between 1 kg/cm$^2$G and 150 kg/cm$^2$G; the high-pressure gas and the organic solvent extract have a high-pressure gas/organic solvent extract weight ratio of 0.1/1 to 5/1; and the organic solvent is in an amount which is 2 to 20 times as large as that of a dehydrated organic acid.

18. The process according to claim 1, wherein the high pressure gas is CO$_2$ at a pressure of 5 to 70 kg/cm$^2$G.

19. The process according to claim 17, wherein the high pressure gas is CO$_2$ at a pressure of 5 to 70 kg/cm$^2$G.

* * * * *